(12) United States Patent
Cai et al.

(10) Patent No.: US 10,561,401 B2
(45) Date of Patent: Feb. 18, 2020

(54) SYSTEMS AND METHODS FOR SELECTION AND DISPLAYING OF IMAGES USING AN INTRAVASCULAR ULTRASOUND IMAGING SYSTEM

(71) Applicant: Boston Scientific SciMed, Inc., Maple Grove, MN (US)

(72) Inventors: Anming He Cai, San Jose, CA (US); Wenguang Li, Santa Clara, CA (US); Lewis Jones Thomas, III, Palo Alto, CA (US)

(73) Assignee: Boston Scientific SciMed, Inc., Maple Grove, MN (US)

( * ) Notice: Subject to any disclaimer, the term of this patent is extended or adjusted under 35 U.S.C. 154(b) by 1496 days.

(21) Appl. No.: 14/483,998

(22) Filed: Sep. 11, 2014

(65) Prior Publication Data
US 2015/0073279 A1 Mar. 12, 2015

Related U.S. Application Data

(60) Provisional application No. 61/876,581, filed on Sep. 11, 2013.

(51) Int. Cl.
*A61B 8/00* (2006.01)
*A61B 8/12* (2006.01)
*A61B 8/08* (2006.01)

(52) U.S. Cl.
CPC .......... *A61B 8/5207* (2013.01); *A61B 8/0891* (2013.01); *A61B 8/12* (2013.01);
(Continued)

(58) Field of Classification Search
CPC ................................ A61B 8/12; A61B 8/0891
See application file for complete search history.

(56) References Cited

U.S. PATENT DOCUMENTS 4,413,630 A 11/1983 Anderson et al.
5,497,776 A 3/1996 Yamazaki et al.
(Continued)

FOREIGN PATENT DOCUMENTS

EP 1324070 A1 7/2003
JP 2003325511 A 11/2003

OTHER PUBLICATIONS

Mintz et al., American College of Cardiology Clinical Expert Consensus Document on Standards for Acquisition, Measurement and Reporting of Intravascular Ultrasound Studies (IVUS), Journal of the American College of Cardiology, vol. 37, No. 5, 2001.

*Primary Examiner* — Baisakhi Roy
*Assistant Examiner* — Jason M Ip
(74) *Attorney, Agent, or Firm* — Lowe Graham Jones PLLC; Bruce E. Black (57) ABSTRACT

A method for real-time displaying of cross-sectional images during an intravascular ultrasound (IVUS) imaging procedure includes, during an intravascular ultrasound imaging procedure, receiving electrical signals from at least one transducer in a catheter as the at least one transducer rotates and moves longitudinally along a lumen of a patient blood vessel; during the intravascular ultrasound imaging procedure, processing the received electrical signals to form a series of cross-sectional images that are longitudinally-offset from one another along a length of the lumen; during the intravascular ultrasound imaging procedure, concurrently displaying i) a most recent image and ii) a previous image that is either a) selected by the operator or b) automatically selected as having a maximum or minimum of a selected image characteristic; and, during the intravascular ultrasound imaging procedure, updating the display of the most recent image as a new image from the series of cross-sectional images is processed.

20 Claims, 9 Drawing Sheets

(52) U.S. Cl.
CPC .............. *A61B 8/461* (2013.01); *A61B 8/463* (2013.01); *A61B 8/085* (2013.01); *A61B 8/466* (2013.01); *A61B 8/5223* (2013.01); *A61B 8/5238* (2013.01)

(56) References Cited

U.S. PATENT DOCUMENTS

| | | |
|---|---|---|
| 5,957,846 A | 9/1999 | Chiang et al. |
| 6,210,333 B1 | 4/2001 | Gardner et al. |
| 6,254,540 B1 | 7/2001 | Kikuchi et al. |
| 6,381,350 B1 * | 4/2002 | Klingensmith .... A61B 5/02007 382/128 |
| 6,554,801 B1 * | 4/2003 | Steward ................... A61B 8/12 600/464 |
| 6,945,938 B2 | 9/2005 | Grunwald |
| 7,246,959 B2 | 7/2007 | Nakatani |
| 7,306,561 B2 | 12/2007 | Sathyanarayana |
| 7,831,081 B2 | 11/2010 | Li |
| 2002/0072671 A1 | 6/2002 | Chenal et al. |
| 2003/0073907 A1 | 4/2003 | Taylor |
| 2003/0236443 A1 | 12/2003 | Cespedes et al. |
| 2006/0100522 A1 | 5/2006 | Yuan et al. |
| 2006/0106320 A1 | 5/2006 | Barbato |
| 2006/0173350 A1 | 8/2006 | Yuan et al. |
| 2006/0253028 A1 | 11/2006 | Lam et al. |
| 2007/0016054 A1 | 1/2007 | Cao et al. |
| 2007/0038081 A1 * | 2/2007 | Eck .......................... A61B 6/12 600/437 |
| 2007/0038111 A1 | 2/2007 | Rehrig et al. |
| 2009/0270731 A1 | 10/2009 | Sathyanarayana |
| 2011/0123087 A1 | 5/2011 | Nie et al. |
| 2012/0130242 A1 | 5/2012 | Burgess et al. |

* cited by examiner

SYSTEMS AND METHODS FOR SELECTION AND DISPLAYING OF IMAGES USING AN INTRAVASCULAR ULTRASOUND IMAGING SYSTEM

CROSS-REFERENCE TO RELATED APPLICATIONS

This application claims the benefit under 35 U.S.C. § 119(e) of U.S. Provisional Patent Application Ser. No. 61/876,581, filed Sep. 11, 2013, which is incorporated herein by reference.

TECHNICAL FIELD

The present invention is directed to the area of imaging systems that are insertable into a patient and methods of making and using the imaging systems. The present invention is also directed to imaging systems configured and arranged to select and concurrently display a plurality of cross-sectional images generated along patient vasculature, as well as methods of making and using the imaging systems.

BACKGROUND

Ultrasound devices insertable into patients have proven diagnostic capabilities for a variety of diseases and disorders. For example, intravascular ultrasound ("IVUS") imaging systems have been used as an imaging modality for diagnosing blocked blood vessels and providing information to aid medical practitioners in selecting and placing stents and other devices to restore or increase blood flow. IVUS imaging systems have been used to diagnose atheromatous plaque build-up at particular locations within blood vessels. IVUS imaging systems can be used to determine the existence of an intravascular obstruction or stenosis, as well as the nature and degree of the obstruction or stenosis. IVUS imaging systems can be used to visualize segments of a vascular system that may be difficult to visualize using other intravascular imaging techniques, such as angiography, due to, for example, movement (e.g., a beating heart) or obstruction by one or more structures (e.g., one or more blood vessels not desired to be imaged). IVUS imaging systems can be used to monitor or assess ongoing intravascular treatments, such as angiography and stent placement in real (or almost real) time. Moreover, IVUS imaging systems can be used to monitor one or more heart chambers.

IVUS imaging systems have been developed to provide a diagnostic tool for visualizing a variety is diseases or disorders. An IVUS imaging system can include a control module (with a pulse generator, an image processor, and a monitor), a catheter, and one or more transducers disposed in the catheter. The transducer-containing catheter can be positioned in a lumen or cavity within, or in proximity to, a region to be imaged, such as a blood vessel wall or patient tissue in proximity to a blood vessel wall. The pulse generator in the control module generates electrical pulses that are delivered to the one or more transducers and transformed to acoustic pulses that are transmitted through patient tissue. Reflected pulses of the transmitted acoustic pulses are absorbed by the one or more transducers and transformed to electric pulses. The transformed electric pulses are delivered to the image processor and converted to an image displayable on the monitor.

BRIEF SUMMARY

One embodiment is a method for real-time displaying of cross-sectional images during an intravascular ultrasound (IVUS) imaging procedure. The method includes the following steps: during an intravascular ultrasound imaging procedure, receiving electrical signals from at least one transducer in a catheter as the at least one transducer rotates and moves longitudinally along a lumen of a patient blood vessel; during the intravascular ultrasound imaging procedure, processing the received electrical signals to form a series of cross-sectional images that are longitudinally-offset from one another along a length of the lumen; during the intravascular ultrasound imaging procedure, concurrently displaying i) a most recent image from the series of cross-sectional images and ii) a previous image from the series of cross-sectional images, wherein the previous image is either a) selected by the operator or b) automatically selected as having a maximum or minimum of a selected image characteristic; and during the intravascular ultrasound imaging procedure, updating the display of the most recent image as a new image from the series of cross-sectional images is processed. Another embodiment is a non-transitory computer readable medium having processor-executable instructions, the processor-executable instructions when installed onto a system enable the system to perform actions, including the steps described with the respect to the preceding method. A further embodiment is an intravascular ultrasound system that includes a catheter, a display, and at least one processor coupled to the catheter and the display. The at least one processor is configured and arranged to perform the steps described with respect to the preceding method.

Another embodiment is a method for automatically displaying cross-sectional images of an intravascular ultrasound (IVUS) imaging procedure. The method includes receiving IVUS data representing data obtained at a plurality of sites along a lumen of a patient blood vessel; processing the IVUS data to form a series of cross-sectional images that are longitudinally-offset from one another along a length of the lumen; and automatically selecting, without user intervention, and concurrently displaying i) a minimum lumen image from the set of cross-sectional images and ii) a maximum lumen image selected from at least a subset of the set of cross-sectional images. Yet another embodiment is a non-transitory computer readable medium having processor-executable instructions, the processor-executable instructions when installed onto a system enable the system to perform actions, including the steps described with the respect to the preceding method. A further embodiment is an intravascular ultrasound system that includes a display and at least one processor coupled to the display. The at least one processor is configured and arranged to perform the steps described with respect to the preceding method.

Yet another embodiment is a method of processing intravascular ultrasound images. The method includes obtaining a set of cross-sectional ultrasound images of a lumen of a patient blood vessel; forming a three-dimensional array of the cross-sectional ultrasound images; cutting the three-dimensional array along a plane to form a cut array; replacing all portions of the cut array associated with an interior of the lumen with a fixed value to form a volume view; and displaying the volume view. Another embodiment is a non-transitory computer readable medium having processor-executable instructions, the processor-executable instructions when installed onto a system enable the system to perform actions, including the steps described with the respect to the preceding method. A further embodiment is an intravascular ultrasound system that includes a display and at least one processor coupled to the display. The at least one processor is configured and arranged to perform the steps described with respect to the preceding method.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of imaging systems that are insertable into a patient and methods of making and using the imaging systems. The present invention is also directed to imaging systems configured and arranged to select and concurrently display a plurality of cross-sectional images generated along patient vasculature, as well as methods of making and using the imaging systems.

The methods, systems, and devices described herein may be embodied in many different forms and should not be construed as limited to the embodiments set forth herein. Accordingly, the methods, systems, and devices described herein may take the form of an entirely hardware embodiment, an entirely software embodiment or an embodiment combining software and hardware aspects. The methods described herein can be performed using any type of computing device, such as a computer, that includes a processor or any combination of computing devices where each device performs at least part of the process.

Suitable computing devices typically include mass memory and typically include communication between devices. The mass memory illustrates a type of computer-readable media, namely computer storage media. Computer storage media may include volatile, nonvolatile, removable, non-removable, transitory, and non-transitory media implemented in any method or technology for storage of information, such as computer readable instructions, data structures, program modules, or other data. Examples of computer storage media include RAM, ROM, EEPROM, flash memory, or other memory technology, CD-ROM, digital versatile disks ("DVD") or other optical storage, magnetic cassettes, magnetic tape, magnetic disk storage or other magnetic storage devices, or any other medium which can be used to store the desired information and which can be accessed by a computing device.

Methods of communication between devices or components of a system can include both wired and wireless (e.g., RF, optical, or infrared) communications methods and such methods provide another type of computer readable media; namely communication media. Communication media typically embodies computer-readable instructions, data structures, program modules, or other data in a modulated data signal such as a carrier wave, data signal, or other transport mechanism and include any information delivery media. The terms "modulated data signal," and "carrier-wave signal" includes a signal that has one or more of its characteristics set or changed in such a manner as to encode information, instructions, data, and the like, in the signal. By way of example, communication media includes wired media such as twisted pair, coaxial cable, fiber optics, wave guides, and other wired media and wireless media such as acoustic, RF, infrared, and other wireless media.

Suitable intravascular ultrasound ("IVUS") imaging systems include, but are not limited to, one or more transducers disposed on a distal end of a catheter configured and arranged for percutaneous insertion into a patient. Examples of IVUS imaging systems with catheters are found in, for example, U.S. Pat. Nos. 7,246,959; 7,306,561; and 6,945,938; as well as U.S. Patent Application Publication Nos. 2006/0100522; 2006/0106320; 2006/0173350; 2006/0253028; 2007/0016054; and 2007/0038111; all of which are incorporated herein by reference.

Figure 1:
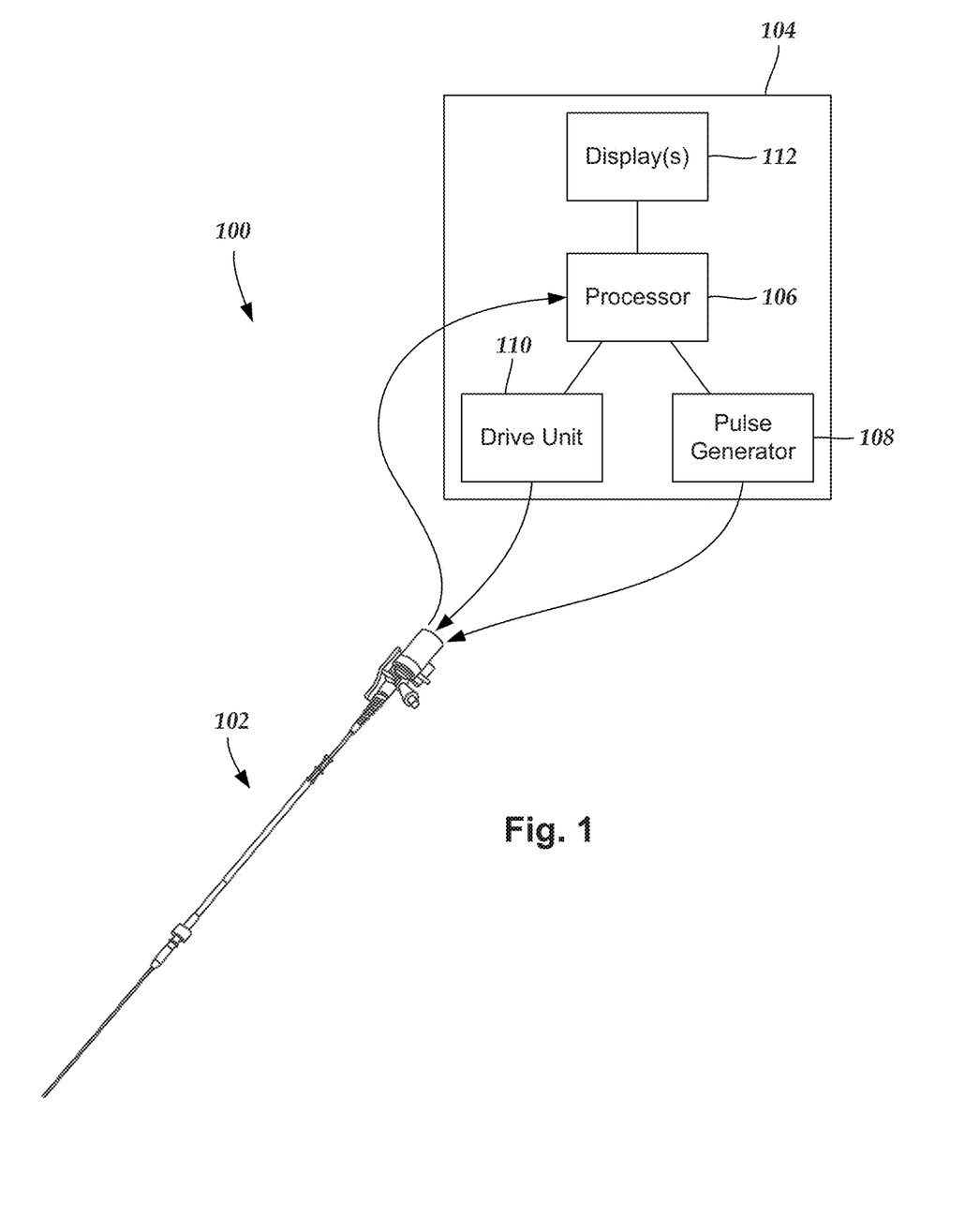
FIG. 1 is a schematic view of one embodiment of an ultrasound imaging system suitable for insertion into a patient, the ultrasound imaging system including a catheter and a control module, according to the invention.

FIG. 1 illustrates schematically one embodiment of an IVUS imaging system 100. The IVUS imaging system 100 includes a catheter 102 that is coupleable to a control module 104. The control module 104 may include, for example, a processor 106, a pulse generator 108, a drive unit 110, and one or more displays 112. In at least some embodiments, the pulse generator 108 forms electric pulses that may be input to one or more transducers (312 in FIG. 3) disposed in the catheter 102.

In at least some embodiments, mechanical energy from the drive unit 110 may be used to drive an imaging core (306 in FIG. 3) disposed in the catheter 102. In at least some embodiments, electric signals transmitted from the one or more transducers (312 in FIG. 3) may be input to the processor 106 for processing. In at least some embodiments, the processed electric signals from the one or more transducers (312 in FIG. 3) can be displayed as one or more images on the one or more displays 112. For example, a scan converter can be used to map scan line samples (e.g., radial scan line samples, or the like) to a two-dimensional Cartesian grid to display the one or more images on the one or more displays 112.

In at least some embodiments, the processor 106 may also be used to control the functioning of one or more of the other components of the control module 104. For example, the processor 106 may be used to control at least one of the frequency or duration of the electrical pulses transmitted from the pulse generator 108, the rotation rate of the imaging core (306 in FIG. 3) by the drive unit 110, the velocity or length of the pullback of the imaging core (306 in FIG. 3) by the drive unit 110, or one or more properties of one or more images formed on the one or more displays 112.

Figure 2:
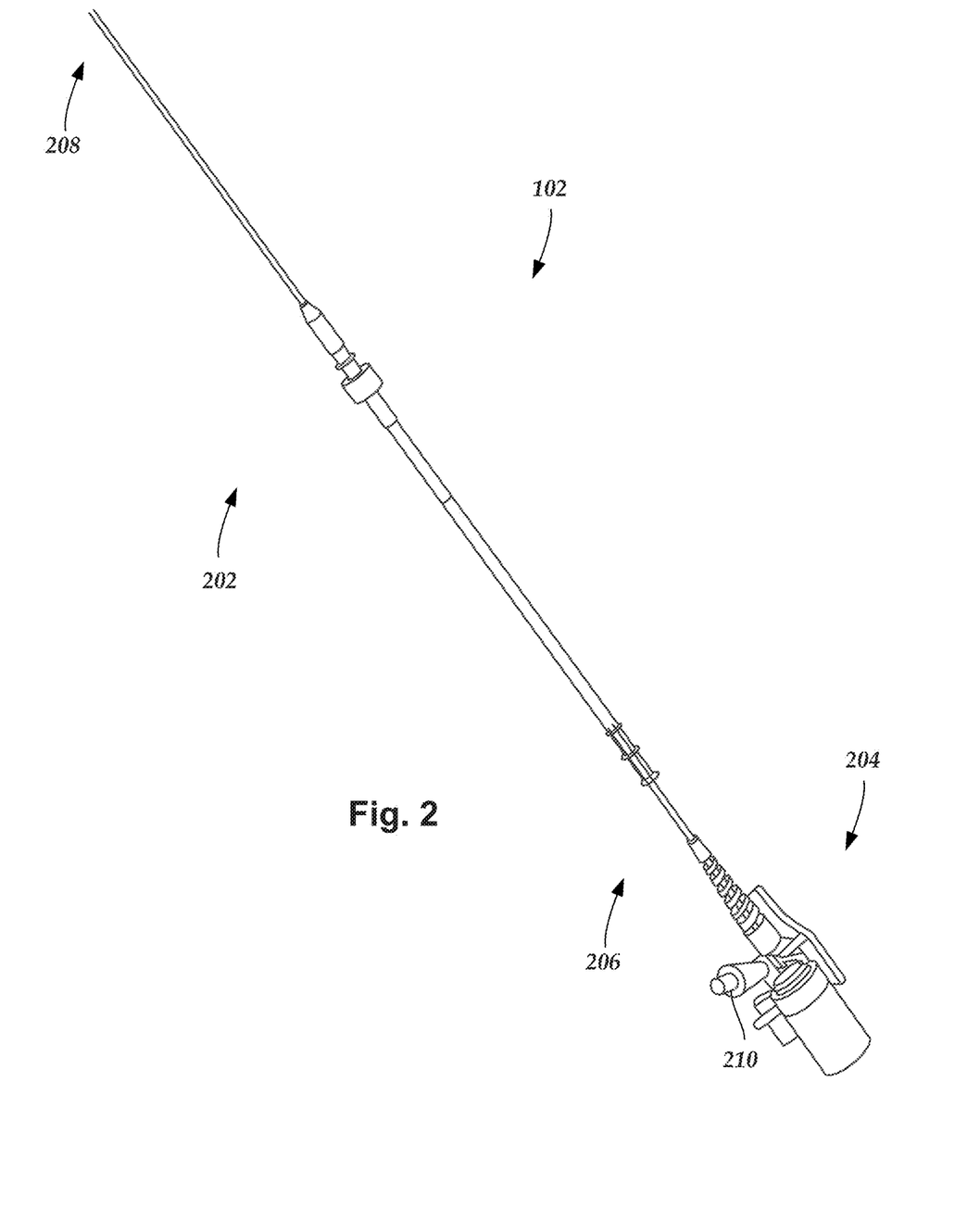
FIG. 2 is a schematic side view of one embodiment of the catheter of FIG. 1, according to the invention.

FIG. 2 is a schematic side view of one embodiment of the catheter 102 of the IVUS imaging system (100 in FIG. 1). The catheter 102 includes an elongated member 202 and a hub 204. The elongated member 202 includes a proximal end 206 and a distal end 208. In FIG. 2, the proximal end 206 of the elongated member 202 is coupled to the catheter huh 204 and the distal end 208 of the elongated member is configured and arranged for percutaneous insertion into a patient. Optionally, the catheter 102 may define at least one flush port, such as flush port 210. The flush port 210 may be defined in the hub 204. The hub 204 may be configured and arranged to couple to the control module (104 in FIG. 1). In some embodiments, the elongated member 202 and the hub 204 are formed as a unitary body. In other embodiments, the elongated member 202 and the catheter hub 204 are formed separately and subsequently assembled together.

Figure 3:
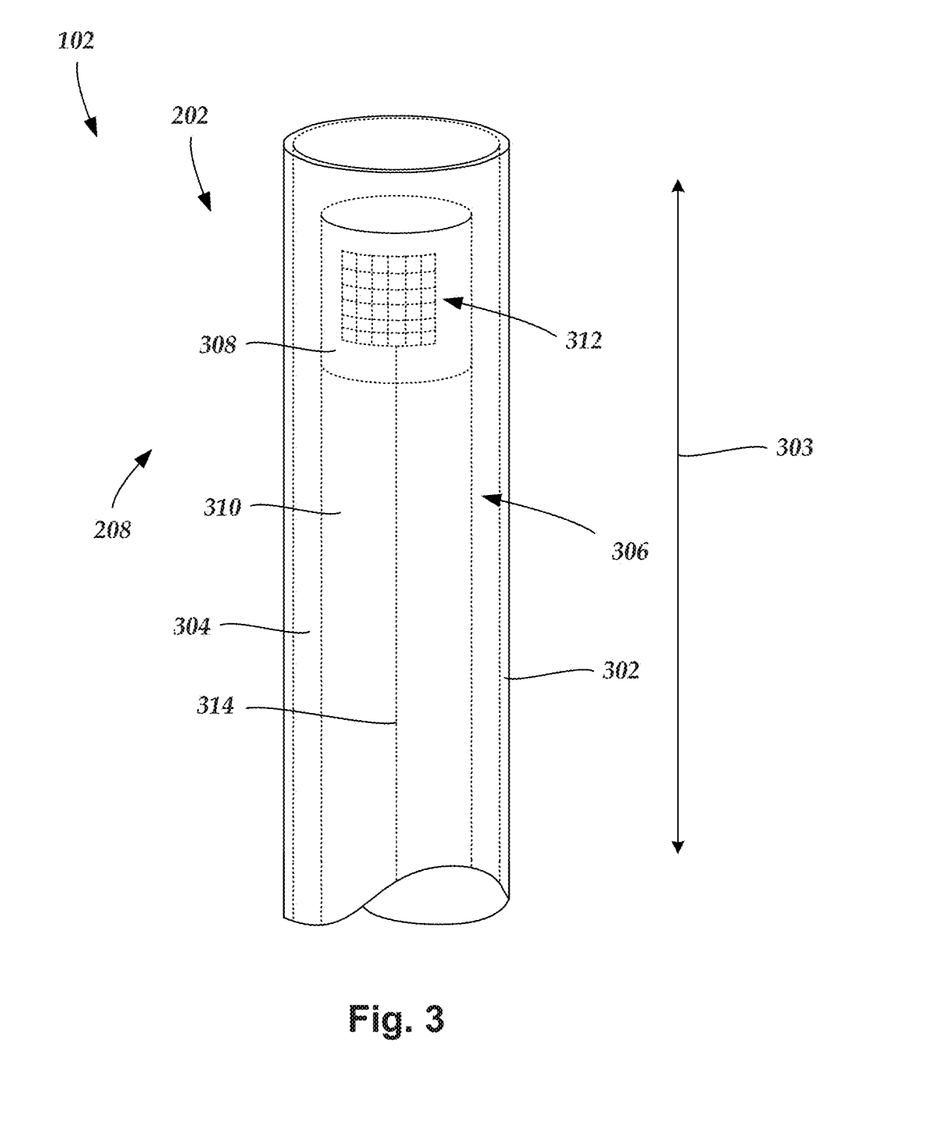
FIG. 3 is a schematic longitudinal cross-sectional view of one embodiment of a distal end of the catheter of FIG. 1 with an imaging core disposed in a lumen defined in the catheter, according to the invention.

FIG. 3 is a schematic perspective view of one embodiment of the distal end 208 of the elongated member 202 of the catheter 102. The elongated member 202 includes a sheath 302 with a longitudinal axis 303 and a lumen 304. An imaging core 306 is disposed in the lumen 304. The imaging core 306 includes an imaging device 308 coupled to a distal end of a driveshaft 310 that is rotatable either manually or using a computer-controlled drive mechanism. One or more transducers 312 may be mounted to the imaging device 308 and employed to transmit and receive acoustic signals. The sheath 302 may be formed from any flexible, biocompatible material suitable for insertion into a patient. Examples of suitable materials include, for example, polyethylene, polyurethane, plastic, spiral-cut stainless steel, nitinol hypotube, and the like or combinations thereof.

In a preferred embodiment (as shown in FIG. 3), an array of transducers 312 are mounted to the imaging device 308. In alternate embodiments, a single transducer may be employed. Any suitable number of transducers 312 can be used. For example, there can be two, three, four, five, six, seven, eight, nine, ten, twelve, fifteen, sixteen, twenty, twenty-five, fifty, one hundred, five hundred, one thousand, or more transducers. As will be recognized, other numbers of transducers may also be used. When a plurality of transducers 312 are employed, the transducers 312 can be configured into any suitable arrangement including, for example, an annular arrangement, a rectangular arrangement, or the like.

The one or more transducers 312 may be formed from one or more known materials capable of transforming applied electrical pulses to pressure distortions on the surface of the one or more transducers 312, and vice versa. Examples of suitable materials include piezoelectric ceramic materials, piezocomposite materials, piezoelectric plastics, barium titanates, lead zirconate titanates, lead metaniobates, polyvinylidenefluorides, and the like. Other transducer technologies include composite materials, single-crystal composites, and semiconductor devices (e.g., capacitive micromachined ultrasound transducers ("cMUT"), piezoelectric micromachined ultrasound transducers ("pMUT"), or the like)

The pressure distortions on the surface of the one or more transducers 312 form acoustic pulses of a frequency based on the resonant frequencies of the one or more transducers 312. The resonant frequencies of the one or more transducers 312 may be affected by the size, shape, and material used to form the one or more transducers 312. The one or more transducers 312 may be formed in any shape suitable for positioning within the catheter 102 and for propagating acoustic pulses of a desired frequency in one or more selected directions. For example, transducers may be disc-shaped, block-shaped, rectangular-shaped, oval-shaped, and the like. The one or more transducers may be formed in the desired shape by any process including, for example, dicing, dice and fill, machining, microfabrication, and the like.

As an example, each of the one or more transducers 312 may include a layer of piezoelectric material sandwiched between a matching layer and a conductive backing material formed from an acoustically absorbent material (e.g., an epoxy substrate with tungsten particles). During operation, the piezoelectric layer may be electrically excited to cause the emission of acoustic pulses.

The one or more transducers 312 can be used to form a radial cross-sectional image of a surrounding space. Thus, for example, when the one or more transducers 312 are disposed in the catheter 102 and inserted into a blood vessel of a patient, the one more transducers 312 may be used to form an image of the walls of the blood vessel and tissue surrounding the blood vessel.

The imaging core 306 is rotated about the longitudinal axis 303 of the catheter 102. As the imaging core 306 rotates, the one or more transducers 312 emit acoustic signals in different radial directions (i.e., along different radial scan lines). For example, the one or more transducers 312 can emit acoustic signals at regular (or irregular) increments, such as 256 radial scan lines per revolution, or the like. It will be understood that other numbers of radial scan lines can be emitted per revolution, instead.

When an emitted acoustic pulse with sufficient energy encounters one or more medium boundaries, such as one or more tissue boundaries, a portion of the emitted acoustic pulse is reflected back to the emitting transducer as an echo pulse. Each echo pulse that reaches a transducer with sufficient energy to be detected is transformed to an electrical signal in the receiving transducer. The one or more transformed electrical signals are transmitted to the control module (104 in FIG. 1) where the processor 106 processes the electrical-signal characteristics to form a displayable image of the imaged region based, at least in part, on a collection of information from each of the acoustic pulses transmitted and the echo pulses received. In at least some embodiments, the rotation of the imaging core 306 is driven by the drive unit 110 disposed in the control module (104 in FIG. 1). In alternate embodiments, the one or more transducers 312 are fixed in place and do not rotate. In which case, the driveshaft 310 may, instead, rotate a mirror that reflects acoustic signals to and from the fixed one or more transducers 312.

When the one or more transducers 312 are rotated about the longitudinal axis 303 of the catheter 102 emitting acoustic pulses, a plurality of images can be formed that collectively form a radial cross-sectional image (e.g., a tomographic image) of a portion of the region surrounding the one or more transducers 312, such as the walls of a blood vessel of interest and tissue surrounding the blood vessel. The radial cross-sectional image can, optionally, be displayed on one or more displays 112. The at least one of the imaging core 306 can be either manually rotated or rotated using a computer-controlled mechanism.

The imaging core 306 may also move longitudinally along the blood vessel within which the catheter 102 is inserted so that a plurality of cross-sectional images may be formed along a longitudinal length of the blood vessel. During an imaging procedure the one or more transducers 312 may be retracted (i.e., pulled back) along the longitudinal length of the catheter 102. The catheter 102 can include at least one telescoping section that can be retracted during pullback of the one or more transducers 312. In at least some embodiments, the drive unit 110 drives the pullback of the imaging core 306 within the catheter 102. The drive unit 110 pullback distance of the imaging core can be any suitable distance including, for example, at least 5 cm, 10 cm, 15 cm, 20 cm, 25 cm, or more. The entire catheter 102 can be retracted during an imaging procedure either with or without the imaging core 306 moving longitudinally independently of the catheter 102.

A stepper motor may, optionally, be used to pull back the imaging core 306. The stepper motor can pull back the imaging core 306 a short distance and stop long enough for the one or more transducers 306 to capture an image or series of images before pulling back the imaging core 306 another short distance and again capturing another image or series of images, and so on.

The quality of an image produced at different depths from the one or more transducers 312 may be affected by one or more factors including, for example, bandwidth, transducer focus, beam pattern, as well as the frequency of the acoustic pulse. The frequency of the acoustic pulse output from the one or more transducers 312 may also affect the penetration depth of the acoustic pulse output from the one or more transducers 312. In general, as the frequency of an acoustic pulse is lowered, the depth of the penetration of the acoustic pulse within patient tissue increases. In at least some embodiments, the IVUS imaging system 100 operates within a frequency range of 5 MHz to 100 MHz.

One or more conductors 314 can electrically couple the transducers 312 to the control module 104 (see e.g., FIG. 1). In which case, the one or more conductors 314 may extend along a longitudinal length of the rotatable driveshaft 310.

The catheter 102 with one or more transducers 312 mounted to the distal end 208 of the imaging core 308 may be inserted percutaneously into a patient via an accessible blood vessel, such as the femoral artery, femoral vein, or jugular vein, at a site remote from the selected portion of the selected region, such as a blood vessel, to be imaged. The catheter 102 may then be advanced through the blood vessels of the patient to the selected imaging site, such as a portion of a selected blood vessel.

An image or image frame ("frame") can be generated each time one or more acoustic signals are output to surrounding tissue and one or more corresponding echo signals are received by the imager 308 and transmitted to the processor 106. Alternatively, an image or image frame can be a composite of scan lines from a full or partial rotation of the imaging core or device. A plurality (e.g., a sequence) of frames may be acquired over time during any type of movement of the imaging device 308. For example, the frames can be acquired during rotation and pullback of the imaging device 308 along the target imaging location. It will be understood that frames may be acquired both with or without rotation and with or without pullback of the imaging device 308. Moreover, it will be understood that frames may be acquired using other types of movement procedures in addition to, or in lieu of, at least one of rotation or pullback of the imaging device 308.

In at least some embodiments, when pullback is performed, the pullback may be at a constant rate, thus providing a tool for potential applications able to compute longitudinal vessel/plaque measurements. In at least some embodiments, the imaging device 308 is pulled back at a constant rate of at least 0.3 mm/s. In at least some embodiments, the imaging device 308 is pulled back at a constant rate of at least 0.4 mm/s. In at least some embodiments, the imaging device 308 is pulled back at a constant rate of at least 0.5 mm/s. In at least some embodiments, the imaging device 308 is pulled back at a constant rate of at least 0.6 mm/s. In at least some embodiments, the imaging device 308 is pulled back at a constant rate of at least 0.7 mm/s. In at least some embodiments, the imaging device 308 is pulled back at a constant rate of at least 0.8 mm/s.

In at least some embodiments, the one or more acoustic signals are output to surrounding tissue at constant intervals of time. In at least some embodiments, the one or more corresponding echo signals are received by the imager 308 and transmitted to the processor 106 at constant intervals of time. In at least some embodiments, the resulting frames are generated at constant intervals of time.

At least some conventional IVUS imaging systems display only a single (e.g., cross-sectional, longitudinal, or the like) image during, or after, an IVUS procedure, such as a pull-back procedure. It may, however, be useful to concurrently display, in real-time during the IVUS procedure (e.g., a pull-back procedure), at least two images, such as the most recently processed image and a previously-obtained image that has some particular or selected image characteristic (e.g., maximum or minimum lumen area or diameter).

Figure 4:
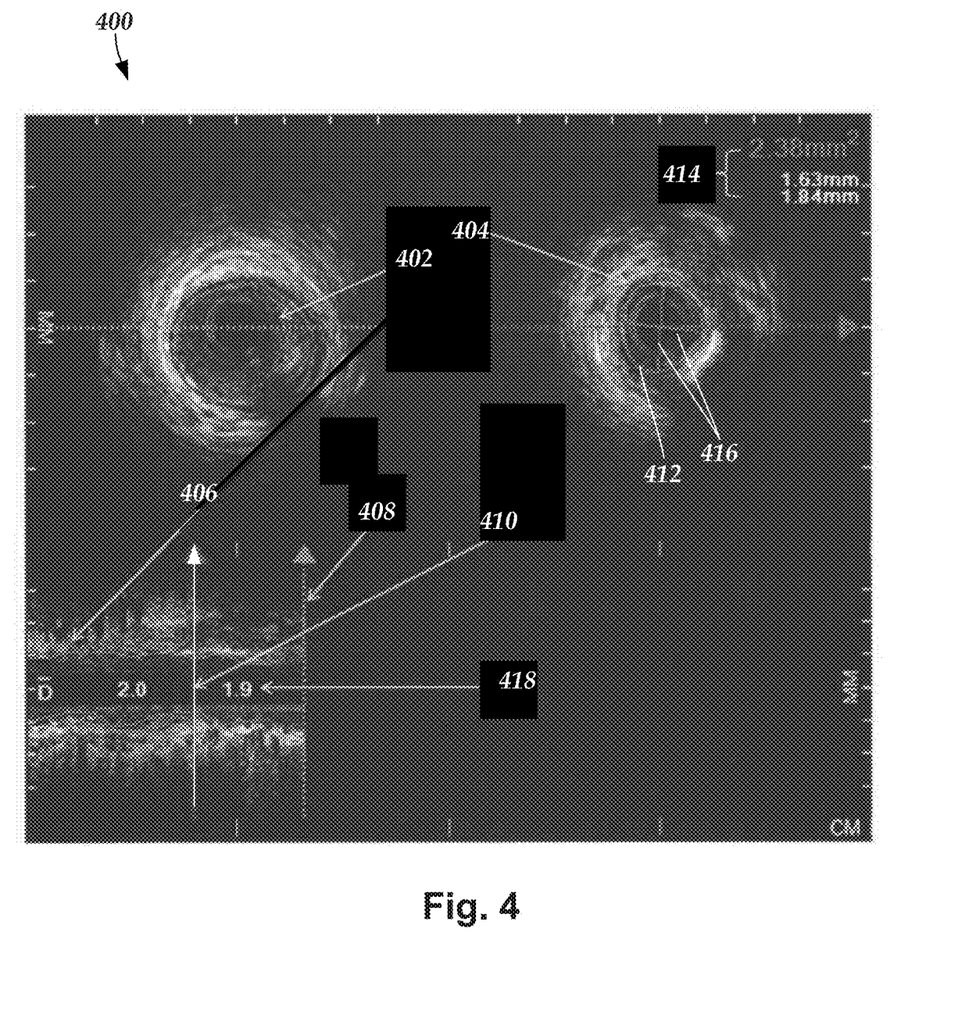
FIG. 4 is a schematic view of one embodiment of a display for the ultrasound imaging system of FIG. 1, the display concurrently showing, during an imaging procedure, a longitudinal view of at least a portion of an imaging run and several cross-sectional images generated from different positions along the longitudinal view, according to the invention.

FIG. 4 is illustrates one embodiment of a display 400 presented during an IVUS procedure, such as a pull-back procedure. The display 400 includes a first cross-sectional image 402 of the most recently (or at least a recently) processed image, a second cross-sectional image 404 that is automatically selected based on an image characteristic, and a longitudinal view 406 based on the images processed to that time. The longitudinal view 406 can be a composite of the processed cross-sectional views taken along a plane perpendicular to the plane of the cross-sectional views. In some embodiments, the longitudinal view 406 can be rotated by rotating the plane of the longitudinal view.

The display 400 can be updated with each new processed image. Such updating can include replacing first cross-sectional image 402 with the most recent image and updating the longitudinal view 406. In some embodiments, the second cross-sectional image 404 can also be updated if there is a new image that has the selected image characteristic (e.g., a maximum or minimum lumen area or diameter.)

Any suitable image characteristic can be used for automatically selecting the second cross-sectional image. Examples of image characteristics include, but are not limited to, lumen area, lumen diameter, average lumen diameter, or even combinations of these image characteristics. In at least some embodiments, the second cross-sectional image is selected as the image with a minimum or maximum of the image characteristic with respect to all of the images that have been processed up to the time of display. In at least some embodiments, the user can select the desired image characteristic and whether a maximum or minimum of that characteristic is desired. In some embodiments, the user can select the image characteristic prior to the imaging run. In other embodiments, the user can even select the image characteristic during the imaging run and, when a different image characteristic is selected, the display 400 is updated with a new second cross-sectional image based on the newly selected image characteristic.

In at least some embodiments, the longitudinal view 406 includes one or more markers 408 and 410 indicating the position of the first and second cross-sectional images 402 and 404, respectively, along the longitudinal view 406. Any suitable shape or symbol can be used for the markers 408, 410. In FIG. 4, the markers 408, 410 are shown as vertical lines. In FIG. 4, the marker 408 is positioned at the current end of the longitudinal view 406, indicating that the first cross-sectional image 402 is the most recent processed image.

As shown in FIG. 4, the display 400 can additionally include imaging information such as, for example, patient information, the length of pullback during an imaging run, the number of image frames generated during an imaging run, the type of catheter used during an imaging run, the date and time of an imaging run, or the like). The display 400 can optionally include one or more identification character(s) associated with one or more of the displayed image frames.

The display 400 can optionally include one or more borders that are provided by border estimation algorithms. For example, a lumen border 412, obtained using a lumen border estimation algorithm, for one or more of the cross-sectional images 402 and 404. The border 412 may be determined by any suitable automated border estimation method or algorithm including, but not limited to, the methods described in U.S. Pat. No. 7,831,081, incorporated herein by reference. In some embodiments, the user may also be permitted to identify or modify the border using any suitable technique including, but not limited to, the techniques described in U.S. Pat. No. 7,831,081.

The display 400 can optionally include a lumen area estimate (in mm$^2$ or any other selected units) and estimates of maximum and minimum lumen diameter (in mm or any other selected units) as indicated with reference numeral 414. These estimates may be made for either (or both) of the cross sectional images 402 and 404. In FIG. 4, the estimates are for cross-sectional image 404 which is the image with the smallest lumen area. In at least some embodiments, the diameters 416 may be indicated on the corresponding cross-sectional image 404. An average lumen diameter 418 (in mm or any other selected units) can also be presented on the longitudinal view 406 for the region of the longitudinal view near the displayed diameter 418.

Figure 5:
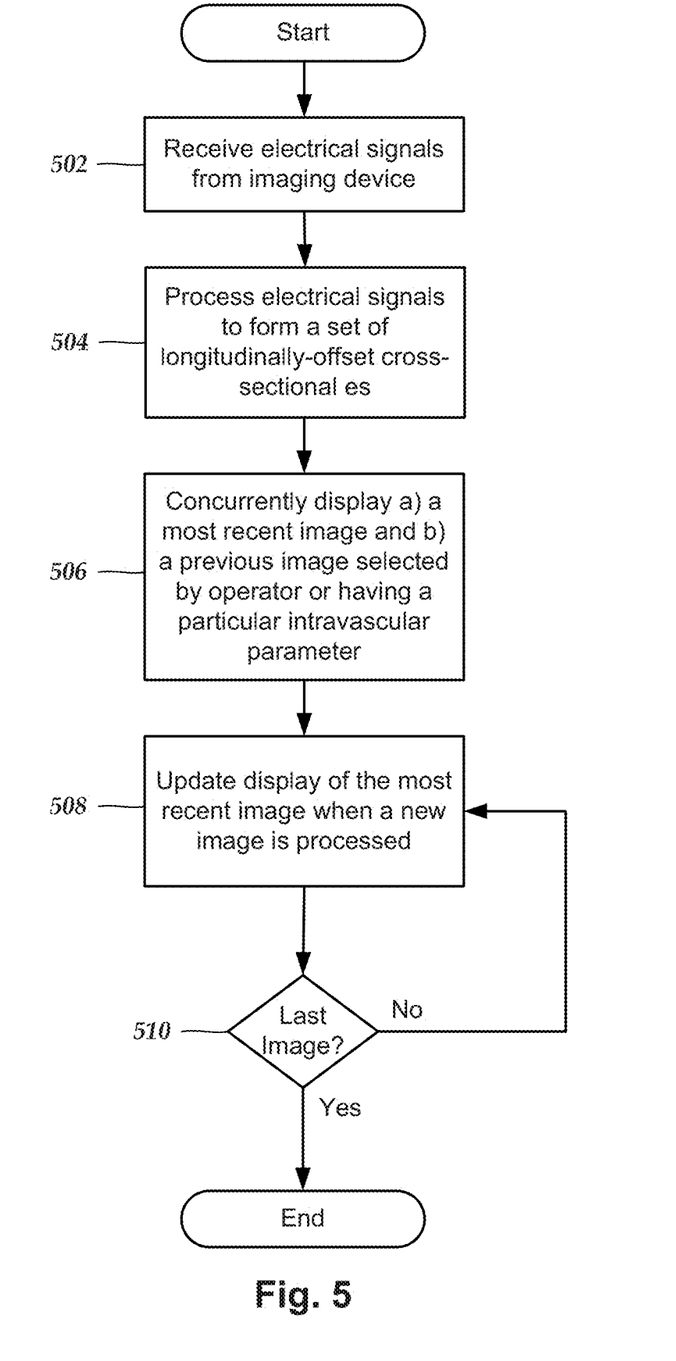
FIG. 5 is a schematic flowchart of one embodiment of a method of real-time displaying of cross-sectional images during an intravascular ultrasound (IVUS) imaging procedure, according to the invention.

FIG. 5 is a flowchart of one embodiment of a method of displaying cross-sectional images during an intravascular ultrasound (IVUS) imaging procedure. Electrical signals are received from an imaging device, such as a transducer (step 502). These electrical signals are processed as they are received to form a set of cross-sectional images (step 504). In at least some embodiments, the images are formed during a pull-back procedure in which the imaging device e.g., a transducer or array of transducers) is pulled back along a blood vessel (e.g., an artery or vein) with imaging occurring at different longitudinal positions along the blood vessel. Such images are longitudinally offset from each other.

During the IVUS procedure, the IVUS system concurrently displays the most recently processed image and a previous cross-sectional image (step 506). The previous cross-sectional image can be user selected or the previous cross-sectional image can be automatically selected based on one or more image characteristics, as described in detail above with respect to the embodiment of FIG. 4. In some embodiments, a longitudinal view is also displayed and may be based on some or all of the cross-sectional images processed up to the time of display. In some of these embodiments, the longitudinal view also includes indicators of the positions along the longitudinal view of the two displayed cross-sectional images.

During the IVUS procedure, as a new cross-sectional image is processed, the display is updated to show the new image as the most recent cross-sectional image (step 608). In at least some embodiment, the previous cross-sectional image may also be updated at user initiation or if a different cross-sectional image is indicated based on one or more image characteristics. In at least some embodiments, the longitudinal view may be updated based on the newly processed cross-sectional image.

The updating of the displayed images continues until the last cross-sectional image is processed (step 510.) When the imaging procedure or run is complete, the display may be altered or updated in accordance with the embodiments described below with respect to FIGS. 6 and 7. One or more steps of this method can be incorporated on a computer-readable medium. Moreover, one or more steps of this method can be performed by a processor that may be part of an IVUS imaging system (see, e.g., processor 106 in FIG. 1) or a separate system.

At least some conventional IVUS imaging systems display only a single (e.g., cross-sectional, longitudinal, or the like) image. It may, however, be useful to concurrently display at least two images that are automatically chosen at the end of a pull-back procure or other imaging run to represent opposite ends of a spectrum of one or more image characteristics, such as the cross-sectional image with minimum lumen area and the cross-sectional image with maximum lumen area (optionally selected from only those images distal to the minimum lumen area image). The automatic selection of these images at the end of the procedure may call up the images that a practitioner is mostly likely interested in viewing or provides a starting point for review of the series of images.

Figure 6:
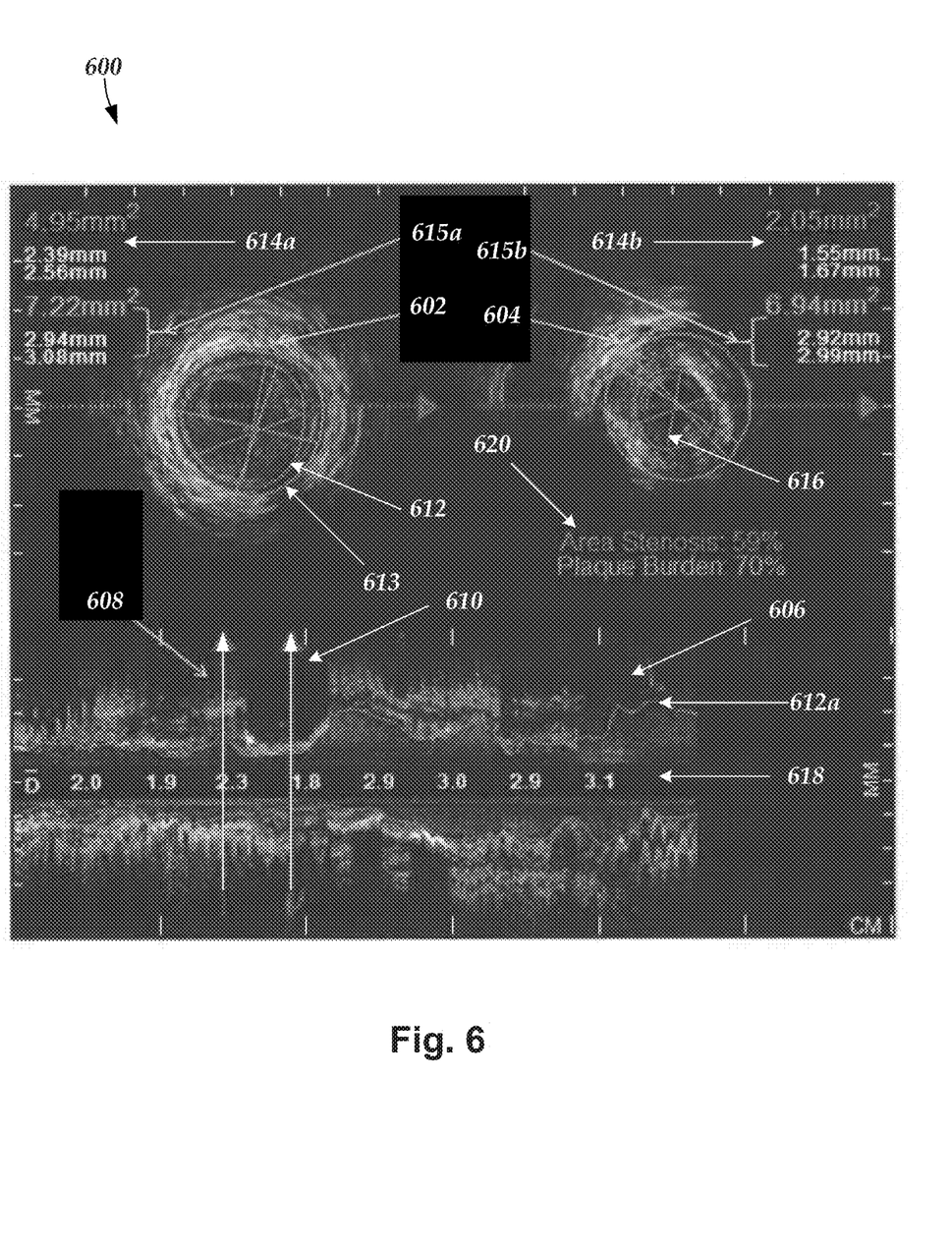
FIG. 6 is a schematic view of another embodiment of a display for the ultrasound imaging system of FIG. 1, the display concurrently showing a longitudinal view of at least a portion of an imaging run and several cross-sectional images generated from different positions along the longitudinal view, according to the invention.

FIG. 6 illustrates one embodiment of a display 600 that includes a first cross-sectional image 602, a second cross-sectional image 604, and a longitudinal view 606 based on the images processed to that time. At the end of an IVUS pull-back procedure or other imaging run or procedure, the first and second cross-sectional images 602, 604 are automatically selected based on one or more imaging characteristics. This automatic selection does not require user intervention at the end of the procedure or imaging run, but may include user input prior to, or during, the procedure or imaging run to select the one or more imaging characteristics. After the automatic selection and display of the first and second cross-sectional images 602, 604, the displayed images may be altered or different images selected by the user.

Any suitable image characteristic can be used for automatically selecting the first and second cross-sectional images. Examples of image characteristics include, but are not limited to, lumen area, lumen diameter, average lumen diameter, or even combinations of these image characteristics. In at least some embodiments, the first and second cross-sectional images are selected to be on opposite ends of a spectrum of a particular image characteristic(s). For example, the first and second cross-sectional images may correspond to an image with a maximum lumen area (or diameter) and an image with a minimum lumen area (or diameter), respectively. The second cross-sectional image is likely to be an image with a substantial amount of plaque or other medical conditions or disease. The first cross-sectional image can be a reference to which the first cross-sectional image is compared.

In some embodiments, the first or second cross-sectional image may not be selected from the full set of images, but rather from a subset of images. For example, in the embodiment of FIG. 6, the second cross-sectional image 604 (with minimum lumen area) is selected first and then the first cross-sectional image 602 is selected from the subset of images distal (i.e., before) the second cross-sectional image 604. It will be understood that other embodiments might select a first cross-sectional from a subset of images proximal (i.e., after) the second cross-sectional image or any other suitable method of arrangement for selecting images.

In at least some embodiments, the user can select the desired image characteristic(s). In some embodiments, the user can select the image characteristic prior to, or during, the imaging procedure or run.

In at least some embodiments, the longitudinal view 606 includes one or more markers 608 and 610 indicating the position of the first and second cross-sectional images 602 and 604, respectively, along the longitudinal view 606. Any suitable shape or symbol can be used for the markers 608, 610. In FIG. 6, the markers 608, 610 are shown as vertical lines.

The display 600 can additionally include imaging information such as, for example, patient information, the length of pullback during an imaging run, the number of image frames generated during an imaging run, the type of catheter used during an imaging run, the date and time of an imaging run, or the like). The display 600 can optionally include one or more identification character(s) associated with one or more of the displayed image frames.

The display 600 can optionally include one or more borders that are provided by border estimation algorithms. For example, a lumen border 612, obtained using a lumen border estimation algorithm, for one or more of the cross-sectional images 602 and 604. The border 612 may be determined by any suitable automated border estimation method or algorithm including, but not limited to, the methods described in U.S. Pat. No. 7,831,081, incorporated herein by reference. In some embodiments, the user may also be permitted to identify or modify the border using any suitable technique including, but not limited to, the techniques described in U.S. Pat. No. 7,831,081.

The display 600 can optionally include an area estimate and estimates of maximum and minimum lumen diameter as indicated with reference numerals 614a, 614b, respectively. In FIG. 6, two diameter measures are provided and correspond to the largest and smallest diameter for the border lumen for the respective cross-sectional image. These estimates may be made for either (or both) of the cross sectional images 602 and 604. In at least some embodiments, the diameters 616 of the lumen border may be indicated on the corresponding cross-sectional image. An average lumen diameter 618 can also be presented on the longitudinal view 606 for the region of the longitudinal view near the displayed diameter 618. In at least some embodiments, other borders, such as the external elastin media (EEM) border 613, can be determined using any suitable method and displayed. Information about the area within the other border(s) and the diameters (largest and smallest) of such border(s) can be included on the display such as illustrated at reference numerals 615a, 615b, respectively.

The display can also include other information. For example, reference numeral 620 points to information labeled as "Area Stenosis" and "Plaque Burden". In some embodiments, Area Stenosis can be calculated as (1−(minimum lumen area/maximum lumen area))*100% where the minimum and maximum lumen areas (reference numerals 614b, 614a) are obtained from the second and first cross-sectional images 604, 602, respectively. In some embodiments, plaque burden can be calculated as (1−(minimum EEM area/maximum EEM area))*100% where the minimum and maximum EEM areas (reference numerals 615b, 615a) are obtained from the second and first cross-sectional images 604, 602, respectively. Other methods of calculating area stenosis and plaque burden, or similar parameters, can also be used.

After the initial display of the first and second cross-sectional views, the user may be permitted to modify the display. For example, the user may be permitted to select different cross-sectional images. The user may be permitted to rescale the cross-sectional images or longitudinal view or to highlight or zoom into a portion of the image/view. The user may be permitted to rotate the longitudinal view or cross-sectional images. The longitudinal view generally corresponds to the intersection of a selected plane with the set of cross-sectional images and so the longitudinal view can be rotated by rotating the selected plane. The user may be permitted to modify any of the borders displayed on the images/views. It will be understood that this is not an exhaustive list of other actions that the user may perform to modify the display.

Figure 7:
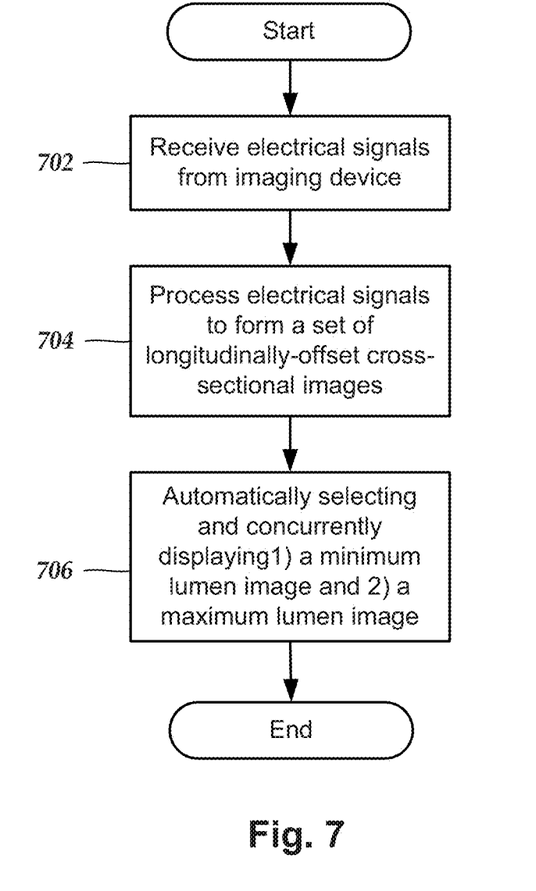
FIG. 7 is a schematic flowchart of one embodiment of a method of automatically displaying cross-sectional images of an intravascular ultrasound (IVUS) imaging procedure, according to the invention.

FIG. 7 is a flowchart of one embodiment of a method of automatically selecting and displaying cross-sectional images after an intravascular ultrasound (IVUS) imaging procedure. Electrical signals are received from an imaging device, such as a transducer (step 702). These electrical signals are processed to form a set of cross-sectional images (step 704). In at least some embodiments, the images are formed during a pull-back procedure in which the imaging device (e.g., a transducer) is pulled back along a blood vessel (e.g., an artery or vein) with imaging occurring at different longitudinal positions along the blood vessel. Such images are longitudinally offset from each other.

After the IVUS procedure is completed, the IVUS system selects, without user intervention, and concurrently displays two cross-sectional images (step 706). For example, the two cross-sectional images can be a minimum lumen image and a maximum lumen image, as described above with respect to the embodiment illustrated in FIG. 6. All of the considerations and parameters discussed above with respect to the selection of first and second cross-sectional images 602, 604 can apply to this embodiment as well. One or more steps of this method can be incorporated on a computer-readable medium. Moreover, one or more steps of this method can be performed by a processor that may be part of an IVUS imaging system (see, e.g., processor 106 in FIG. 1) or a separate system.

The images obtained from an IVUS procedure can be used to evaluate a blood vessel, such as a vein or artery. In particular, a vessel volume view can be produced that can be useful to display the inside wall of the body lumen. In some embodiments, a longitudinal cut plane can be defined and the data from the set of cross-sectional views can be cut along the longitudinal cut plane and a longitudinal volume view can be produced. This can also be performed using two or more different longitudinal cut planes.

Figure 8A:
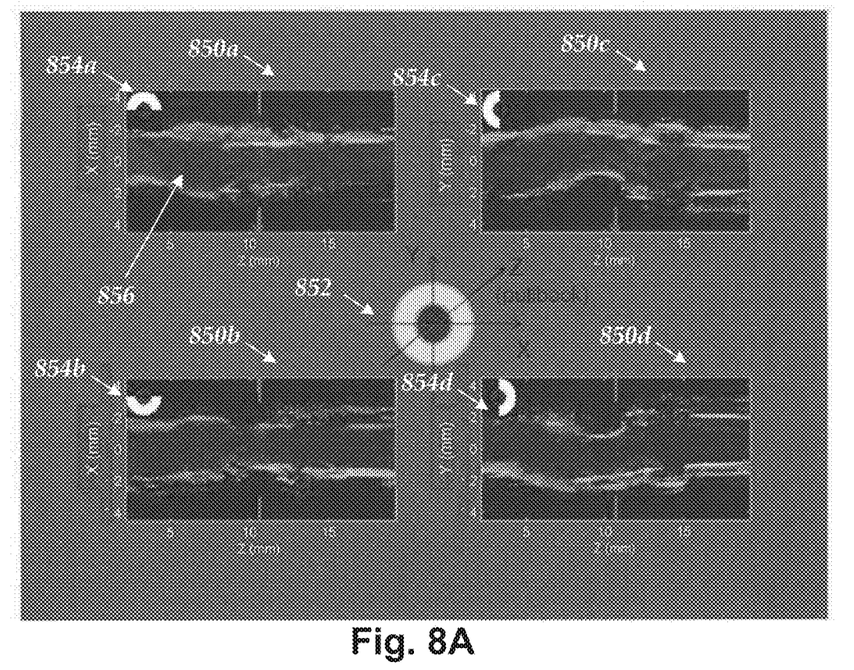
FIG. 8A is a schematic view of a display for the ultrasound imaging system of FIG. 1, the display showing four different volume views where the pixels corresponding to the interior of a body lumen have a uniform gray level, according to the invention.

FIG. 8A illustrates four longitudinal volume views 850a, 850b, 850c, 850d and an illustration 852 of the axes selected for these views. Volume views 850a, 850b are generated with a longitudinal cut plane along the "x-axis" and volume views 850c, 850d are generated with a longitudinal cut plane along the "y-axis". It will be understood that any other suitable cut plane(s) can be used. Each of the volume views includes an illustration 854a, 854b, 854c, 854d, of which part (indicated in white) of the corresponding cross-sectional views forms the volume view.

Figure 8B:
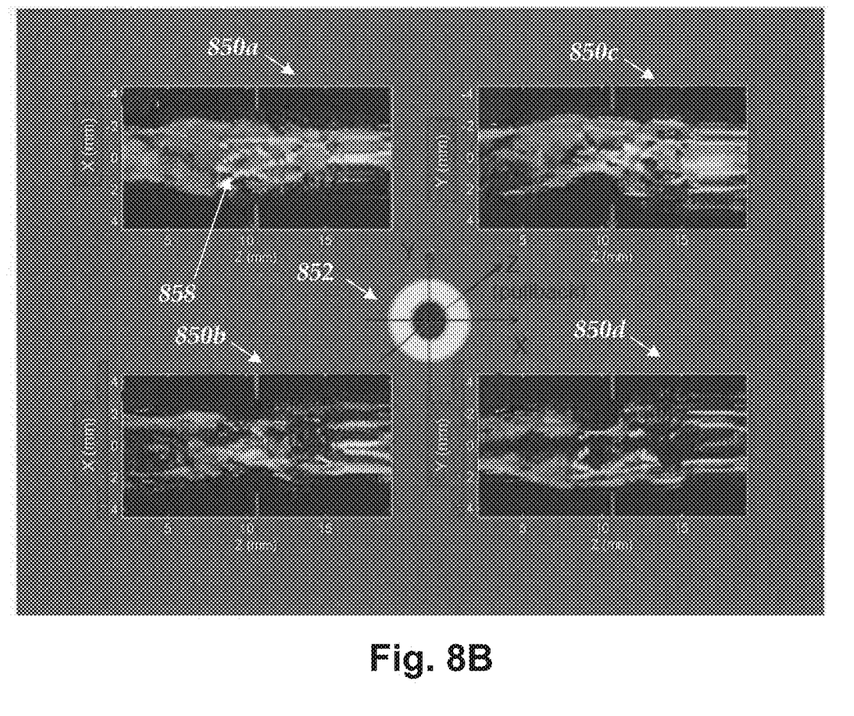
FIG. 8B is a schematic view of a display for the ultrasound imaging system of FIG. 1, the display showing four different volume views where the pixels corresponding to the interior of a body lumen have a uniform gray level that is black or transparent, according to the invention.

Because the display pixels corresponding to the interior of the lumen are often the result of blood scattering, the interior lumen pixels 856 in the volume views of FIG. 8A are set to a fixed brightness, fixed value, fixed gray level, or fixed color. The volume view is then generated using any suitable display technique including, but not limited to, ray tracing (e.g., ray tracing from front to back through the data). FIG. 8B illustrates the same volume views 850a, 850b, 850c, 850d except that the brightness, value, gray level, or color of the interior lumen pixels have been set to black or transparent. In this embodiment, the interior lumen pixels can be effectively erased (or at least partially erased) to more clearly illustrated the lumen walls or even elements such as a stent 858 within the lumen.

Figure 9:
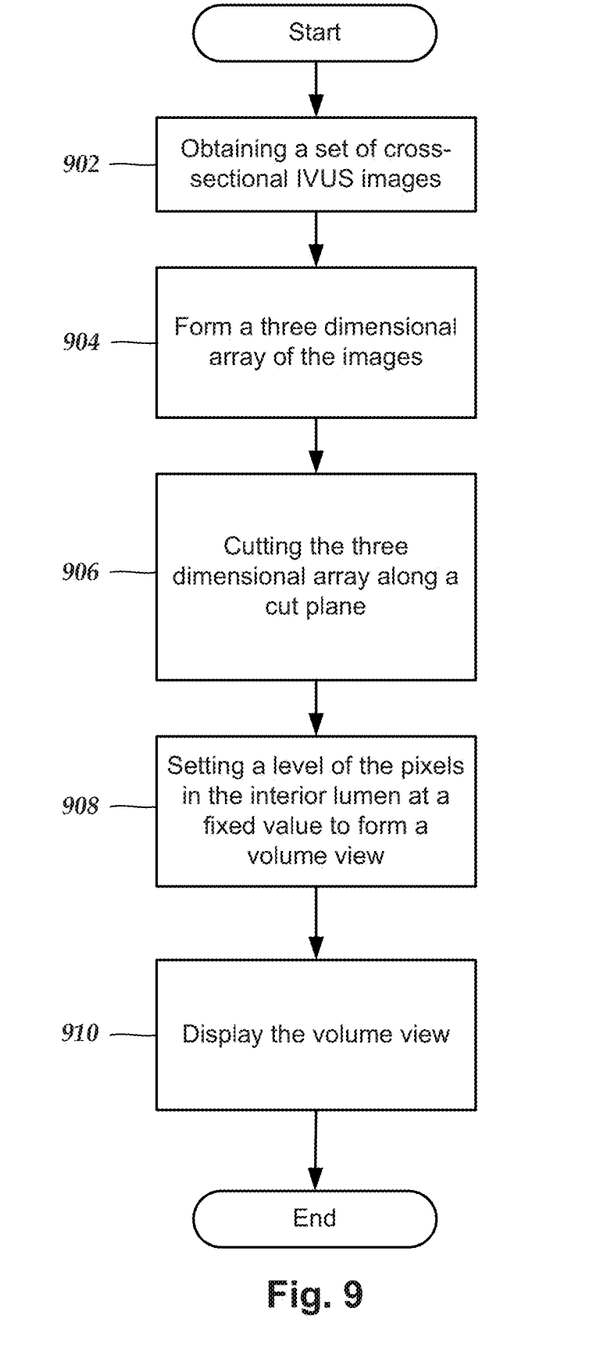
FIG. 9 is a schematic flowchart of one embodiment of a method of processing intravascular ultrasound images to form the volume views of FIGS. 8A and 8B, according to the invention.

FIG. 9 is a flowchart of one embodiment of a method of processing intravascular ultrasound images. The method includes obtaining a set of cross-sectional ultrasound images of a lumen of a patient blood vessel (step 902). These ultrasound images can then be formed into a three-dimensional array (step 904). The three-dimensional array is cut along one or more planes to form a cut array (step 906). All portions of the cut array (e.g., pixels in an image or data representing the pixels) associated with an interior of the lumen with a fixed value to form one or more volume views (step 908). The fixed value can be a fixed brightness, fixed gray level, or fixed color. In some embodiments, the fixed value can result in the pixels being black or transparent. The volume view(s) can then be displayed (step 910).

Any of the images, including, but not limited to, the set of cross-sectional images, the first cross-sectional image, the second cross-sectional image, the longitudinal view, or any other images illustrated in FIGS. 4, 6, and 8, can be saved as one or more files. The saved images may also include the lumen border, markers on the longitudinal view, external elastin media border, and the like or any other items illustrated in FIGS. 4, 6, and 8. In addition, any suitable combination of the image characteristics and other parameters, including, but not limited to, the lumen area, lumen diameter, average lumen area, average lumen diameter, maximum lumen diameter, minimum lumen diameter, area stenosis, plaque burden, and the like or any other items illustrated in FIGS. 4, 6, and 8, can be saved with, in addition to, or separate from, the image(s). The saving of images and other information may be performed automatically or at user-initiation or at any combination thereof.

In at least some embodiments, the saved images and other information can be retrieved and displayed on the system and optionally may be exportable for display on another computer or system. In at least some embodiments, the system or another system with suitable software can replay the imaging run. During this replay (e.g., simulation) of the imaging run, the system may operate similar to the display and method described with respect to FIGS. 4 and 5 and update the displayed images as they become available during the simulation of the imaging run. In at least some embodiments, the system or another system with suitable software can operate similar to the display and method described with respect to FIGS. 6 and 7 and update the displayed images as they are selected by the user.

In at least some embodiments, the displayed images and information, or any subset of images or information, of FIGS. 4, 6, and 8 can be printed. In at least some embodiments, characteristics of images, such as lumen areas or diameters, can be printed or plotted along the longitudinal view at positions that are automatically selected or user-selected or any combination thereof.

It will be understood that each block of the flowchart illustrations, and combinations of blocks in the flowchart illustrations, as well any portion of the tissue classifier, imaging transducer(s), control module, systems and methods disclosed herein, can be implemented by computer program instructions. These program instructions may be provided to a processor to produce a machine, such that the instructions, which execute on the processor, create means for implementing the actions specified in the flowchart block or blocks or described for the tissue classifier, imager, control module, systems and methods disclosed herein. The computer program instructions may be executed by a processor to cause a series of operational steps to be performed by the processor to produce a computer implemented process. The computer program instructions may also cause at least some of the operational steps to be performed in parallel. Moreover, some of the steps may also be performed across more than one processor, such as might arise in a multi-processor computer system. In addition, one or more processes may also be performed concurrently with other processes, or even in a different sequence than illustrated without departing from the scope or spirit of the invention.

The computer program instructions can be stored on any suitable computer-readable medium including, but not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by a computing device.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A method for real-time displaying of cross-sectional images during an intravascular ultrasound (IVUS) imaging procedure, the method comprising:
  during an intravascular ultrasound imaging procedure, receiving electrical signals from at least one transducer in a catheter as the at least one transducer rotates and moves longitudinally along a lumen of a patient blood vessel;
  during the intravascular ultrasound imaging procedure, processing the received electrical signals to form a series of cross-sectional images, wherein the cross-sectional images are longitudinally-offset from one another along a length of the lumen;
  during the intravascular ultrasound imaging procedure, concurrently displaying i) a most recent image from the series of cross-sectional images and ii) a previous image from the series of cross-sectional images, wherein the previous image is either a) selected by a user or b) automatically selected as having a maximum or minimum of a selected image characteristic; and during the intravascular ultrasound imaging procedure, updating the display of the most recent image as a new image from the series of cross-sectional images is processed.

2. The method of claim 1, wherein the previous image is automatically selected as having a minimum lumen area.

3. The method of claim 1, wherein the previous image is automatically selected as having a minimum lumen diameter.

4. The method of claim 1, further comprising, during the intravascular ultrasound imaging procedure, displaying a longitudinal view of the lumen based on the cross-sectional images up to the most recent image.

5. The method of claim 4, wherein updating the display comprises updating the longitudinal view based on the new image.

6. The method of claim 4, further comprising indicating positions of the most recent image and the selected previous image on the longitudinal view.

7. The method of claim 1, further comprising, during the intravascular ultrasound imaging procedure, providing a lumen boundary around the lumen of the selected previous image.

8. The method of claim 7, further comprising, during the intravascular ultrasound imaging procedure, adjusting the lumen boundary according to instructions from a user.

9. The method of claim 1, further comprising
forming a three-dimensional array of the series of cross-sectional images;
cutting the three-dimensional array along a plane to form a cut array;
replacing all portions of the cut three-dimensional array associated with an interior of the lumen with a fixed value to form a volume view; and
displaying the volume view.

10. The method of claim 9, wherein the fixed value is black.

11. The method of claim 9, wherein the fixed value renders the portions of the cut three-dimensional array associated with the interior of the lumen transparent when displayed.

12. The method of claim 9, wherein displaying the volume view comprises rendering the volume view by ray tracing using data of the volume view.

13. The method of claim 2, further comprising displaying a lumen area estimate.

14. The method of claim 3, further comprising displaying a minimum lumen diameter.

15. The method of claim 1, further comprising
upon completion of the intravascular ultrasound imaging procedure, automatically selecting, without user intervention, and concurrently displaying i) a minimum lumen image from the series of cross-sectional images and ii) a maximum lumen image selected from at least a subset of the series of cross-sectional images.

16. The method of claim 15, further comprising displaying a numerical indication of stenosis area.

17. The method of claim 15, further comprising displaying a numerical indication of plaque burden.

18. The method of claim 15, wherein the maximum lumen image is selected from the subset of cross-sectional images obtained prior the minimum lumen image.

19. The method of claim 15, wherein the minimum lumen image is selected based on lumen area.

20. The method of claim 15, further comprising providing a lumen boundary around the lumens of the minimum lumen image and the maximum lumen image.

* * * * *